(12) United States Patent
Gayer et al.

(10) Patent No.: US 6,660,872 B1
(45) Date of Patent: Dec. 9, 2003

(54) METHOD OF PRODUCING METHOXYIMINO ACETIC AMIDE

(75) Inventors: Herbert Gayer, Monheim (DE); Bernd Gallenkamp, Wuppertal (DE); Peter Gerdes, Aachen (DE); Ulrich Heinemann, Leichlingen (DE); Walter Hübsch, Wuppertal (DE); Bernd-Wieland Krüger, Gladbach (DE); Fritz Maurer, Monheim (DE); Holger Weintritt, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/979,213

(22) PCT Filed: May 12, 2000

(86) PCT No.: PCT/EP00/04300

§ 371 (c)(1),
(2), (4) Date: Nov. 21, 2001

(87) PCT Pub. No.: WO00/71504

PCT Pub. Date: Nov. 30, 2000

(30) Foreign Application Priority Data

May 25, 1999 (DE) .......................... 199 23 624
Jan. 11, 2000 (DE) .......................... 100 00 733

(51) Int. Cl.[7] ..................... C07D 307/93; C07C 231/00; C07C 233/00; C07C 235/00; C07C 237/00
(52) U.S. Cl. ..................... 549/466; 549/467; 564/134; 564/167; 564/256; 564/258; 564/265; 560/39
(58) Field of Search ........................ 549/466, 467; 564/256, 258, 265, 134, 167; 560/39

(56) References Cited

U.S. PATENT DOCUMENTS 6,150,521 A * 11/2000 Gayer et al. .................. 544/65
6,235,743 B1 * 5/2001 Gayer et al. .................. 514/269
6,359,133 B2 3/2002 Gayer et al. .................. 544/319
6,479,675 B1 11/2002 Gayer et al. .................. 549/467
2002/0169316 A1 11/2002 Gayer et al. .................. 544/65

FOREIGN PATENT DOCUMENTS

| DE | 195 25 969 | 1/1997 |
| DE | 197 06 399 | 4/1997 |
| DE | 196 46 407 | 5/1998 |
| DE | 196 46 407 A1 * | 5/1998 |
| DE | 197 06 396 | 6/1998 |
| EP | 0 398 692 | 11/1990 |
| EP | 0 846 691 | 6/1998 |
| GB | 2 253 624 | 9/1992 |

OTHER PUBLICATIONS

Proc. Indian Acad. Sci., vol. 83 A, No. 6, 1976, pp. 238–242. Reactivity of 2–Hydroxy–w–nitroactophenones: synthesis of 2–oximinocoumaranones by K. Venkateswara Rao and V. Sudaramurthy.

Farmco Ed. Sci., 28, 1973, pp. 157–159, Ricerche Nel Campo Delle Sostanze Ad Attivita Antivirale by M. Giannella and M. Pignini.

Chem. Ber. 35, pp. 1640–1646, 1902, R. Stoermer aund B. Kahlert: Ueber das 1–Nitrocumaron und eine eigenthumliche Umlagerung desselben.

Beilstein, E II 17, p. 462, Hetero:10 (BZW.S). –DIOXO-.VERBINDUNGEN $C_nH_{2n-10}O_3$, 1952.

Gazzetta Chimica Italiana, vol. LVI, 1926, Mameli Efisio, pp. 759–772.

* cited by examiner

*Primary Examiner*—Mukund J. Shah
*Assistant Examiner*—Zachary C. Tucker
(74) *Attorney, Agent, or Firm*—Raymond J. Harmuth; Richard E. L. Henderson

(57) ABSTRACT

The present invention relates to novel processes for preparing methoxyimino-acetamides.

12 Claims, No Drawings

METHOD OF PRODUCING METHOXYIMINO ACETIC AMIDE

This application is a 371 of PCT/EP00/04300, published May 12, 2000.

The present invention relates to novel processes for preparing methoxyimino-acetamides.

A process for preparing N-methyl-[2-(2-hydroxy)phenyl]-2-methoxyimino-acetamide has already been described (cf. EP 0 398 692 A2). However, the compounds prepared by this process are only obtainable in moderate yields.

It has now been found that according to process part 1) compounds of the formula (I)

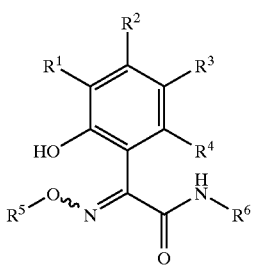

(I)

in which

R$^1$, R$^2$, R$^3$ and R$^4$ are identical or different and independently of one another each represents hydrogen, halogen, cyano, nitro, in each case optionally halogen-substituted alkyl, alkoxy, alkylthio, alkylsulphinyl or alkylsulphonyl, R$^5$ represents substituted or unsubstituted alkyl, R$^6$ represents hydrogen, substituted or unsubstituted alkyl, are obtained when A) according to process step 2), compounds of the formula (IV),

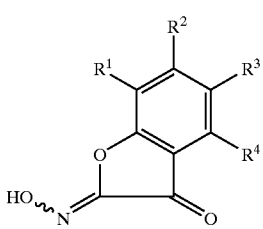

(IV)

in which

R$^1$, R$^2$, R$^3$ and R$^4$ are as defined above, are reacted, in the presence of an acid or an acidic ion exchanger, with an alcohol of the formula (V),

—OH    (V)

in which

R$^7$ represents substituted or unsubstituted alkyl, and with a carbonyl compound, which binds the hydroxylammonium chloride eliminated in the reaction forming an oxime, to give compounds of the formula (VI), (VI)

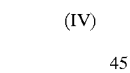

in which

R$^1$, R$^2$, R$^3$, R$^4$ and R$^7$ are as defined above, and the resulting compounds of the formula (VI) are either a) according to process step 3), reacted with a hydroxylammonium salt, if appropriate in the presence of a diluent and if appropriate in the presence of an acid or an acid acceptor, to give compounds of the formula (VII), (VII)

in which

R$^1$, R$^2$, R$^3$, R$^4$ and R$^7$ are as defined above, and the resulting compounds of the formula (VII) are, according to process step 4), reacted with an alkylating agent of the formula (VIII),

R$^5$—X    (VIII)

in which

R$^5$ is as defined above and

X represents halogen, —O—CO—OR$^5$— or —O—SO$_2$—O—R$^5$, where R$^5$ is as defined above, if appropriate in the presence of a diluent and if appropriate in the presence of a base, or b) are, according to process step 5), reacted with an alkoxyamine of the formula (IX),

R$^5$—O—NH$_2$    (IX)

in which

R$^5$ is as defined above,

— or an acid addition complex thereof—, if appropriate in the presence of a diluent and if appropriate in the presence of an acid or an acid acceptor, or when B) according to process step 6), compounds of the formula (IV),

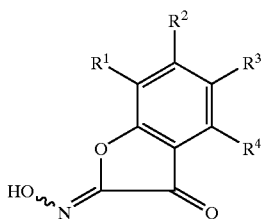

(IV)

in which
$R^1$, $R^2$, $R^3$ and $R^4$ are as defined above,
are reacted with an alkoxyamine of the formula (IX),

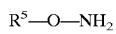  (IX)

in which
$R^5$ is as defined above,
— or an acid addition complex thereof—if appropriate in the presence of a diluent and if appropriate in the presence of an acid,
or when
C) according to process step 7), compounds of formula (IV),

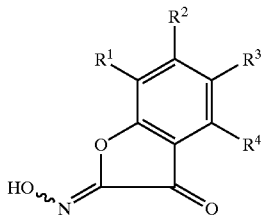

(IV)

in which
$R^1$, $R^2$, $R^3$ and $R^4$ are as defined above,
are reacted, in the presence of an acid or an acidic ion exchanger, with an alcohol of the formula (V),

  (V)

in which $R^7$ is as defined above,
if appropriate with addition of a hydroxylammonium salt,
and the resulting compounds of the formula (VII),

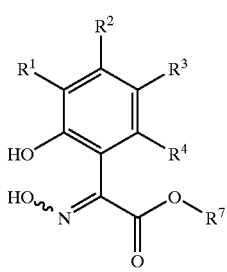

(VII)

in which
$R^1$, $R^2$, $R^3$, $R^4$ and $R^7$ are as defined above,
are reacted according to process step 4),
or when
D) according to process step 8), compounds of the formula (X),

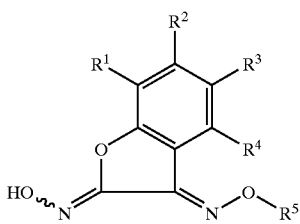

(X)

in which
$R^1$, $R^2$, $R^3$, $R^4$ and $R^5$ are as defined above,
are reacted, in the presence of an acid or an acidic ion exchanger, with an alcohol of the formula (V),

  (V)

in which $R^7$ is as defined above, if appropriate in the presence of a carbonyl compound which binds the hydroxylammonium chloride eliminated in the reaction forming an oxime,
and the compounds of the formula (II) obtained according to processes A)–D),

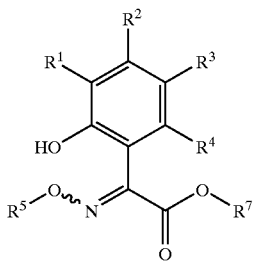

(II)

in which
$R^1$, $R^2$, $R^3$, $R^4$ and $R^5$ are as defined above and
$R^7$ represents unsubstituted or substituted alkyl,
are, if appropriate without intermediate isolation of the compounds of the formula (II) (one-pot process), reacted according to process step 1) with an alkylamine of the formula (III),

  (III)

in which $R^6$ is as defined above, if appropriate in the presence of a diluent.
Moreover, it has been found that, according to process part 2), compounds of the formula (XI),

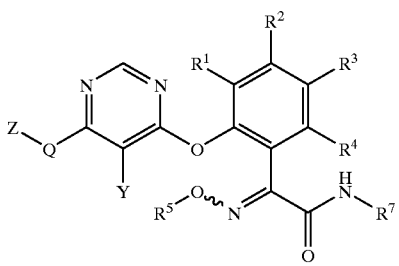

(XI)

in which
Z represents unsubstituted or substituted cycloalkyl, aryl or heterocyclyl, Q represents oxygen or sulphur,
Y represents halogen and
$R^1$, $R^2$, $R^3$, $R^4$, $R^5$ and $R^7$ are as defined above,
are obtained when compounds of the formula (I) are reacted according to the novel process part 1), and these compounds (I) are either
E) according to process step 9) reacted with pyrimidine derivatives of the formula (XII),

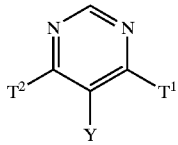

(XII)

in which
$T^1$ and $T^2$ are identical or different and represent halogen or —$SO_2$—$R^8$, where $R^8$ is alkyl, aryl or benzyl, and
Y is as defined above,
if appropriate in the presence of a diluent and if appropriate in the presence of a base, and the resulting compounds of the formula (XIII),

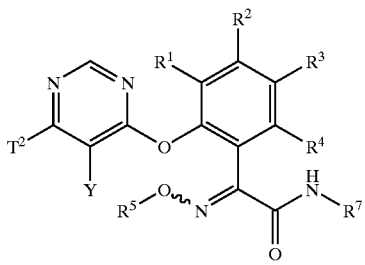

(XIII)

in which
$T^2$, Y, $R^1$, $R^2$, $R^3$, $R^4$, $R^5$ and $R^7$ are as defined above,
are reacted, according to process step 10), with a cyclic compound of the general formula (XIV),

Z—Q—H  (XIV)

in which
Z and Q are as defined above,
if appropriate in the presence of a diluent and if appropriate in the presence of an acid acceptor and if appropriate in the presence of a catalyst, or
F) are reacted according to process step 11) with compounds of the formula (XV),

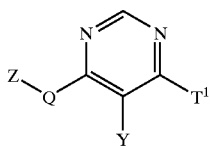

(XV)

in which
Z, Q, $T^1$ and Y are as defined above,
if appropriate in the presence of a diluent and if appropriate in the presence of a base.

Furthermore, it has been found that the Z-isomeric compounds of the formula (XI) are isomerized to E-isomeric compounds of the formula (XI) when Z isomers or E/Z isomer mixtures of the compounds of the formula (XI) are treated with acids, if appropriate in a diluent. The isomerization affords the E isomers in good yields.

Furthermore, it has been found that the Z-isomeric compounds of the formula (XIII) are isomerized to E-isomeric compounds of the formula (XIII) when Z isomers or E/Z isomer mixtures of the compounds of the formula (XIII) are treated with acids, if appropriate in a diluent. The isomerization affords the E isomers in good yields.

In the definitions, the saturated or unsaturated hydrocarbon chains, such as alkyl, alkanediyl, alkenyl or alkinyl, are, including in combination with heteroatoms, such as, for example, in alkoxy, alkylthio or alkylamino, in each case straight-chain or branched having in particular 4 carbon atoms.

Aryl denotes aromatic, mono- or polycyclic hydrocarbons rings, such as, for example, phenyl, naphthyl, anthranyl, phenanthryl, preferably phenyl or naphthyl, in particular phenyl.

Halogen generally denotes fluorine, chlorine, bromine or iodine, preferably fluorine, chlorine or bromine, in particular fluorine or chlorine. Heterocyclyl denotes saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen or sulphur. If appropriate, the cyclic compounds form a polycyclic ring system together with further carbocyclic or heterocyclic fused-on or bridged rings. Preference is given to mono- or bicyclic ring systems, in particular to mono- or bicyclic aromatic ring systems.

Cycloalkyl denotes saturated carbocyclic compounds which may, if appropriate, form a polycyclic ring system with further carbocyclic, fused-on or bridged rings.

Halogenoalkyl denotes partially or fully halogenated alkyl. In the case of polyhalogenated halogenoalkyl, the halogen atoms can be identical or different. Preferred halogen atoms are fluorine and chlorine and in particular fluorine. If the halogenoalkyl also carries other substituents, the maximum number of halogen atoms possible is reduced to the remaining free valencies.

The compounds according to the invention can, if appropriate, be present as mixtures of different possible isomeric forms, in particular of stereoisomers, such as, for example E and Z. What is claimed are both the E and the Z isomers, and any mixtures of these isomers.

In general, Z represents in particular:
cycloalkyl having 3 to 7 carbon atoms which is in each case optionally mono- to disubstituted by halogen, alkyl or hydroxyl;
heterocyclyl having 3 to 7 ring members which is optionally substituted by alkyl having 1 to 4 carbon atoms;
or phenyl or naphthyl, each of which is optionally mono- to tetrasubstituted by identical or different substituents, where the possible substituents are preferably selected from the list below:
halogen, cyano, nitro, amino, hydroxyl, formyl, carboxyl, carbamoyl, thiocarbamoyl;
in each case straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl having 1 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, oxo, methyl, trifluoromethyl and ethyl;

or a grouping

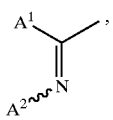

in which
$A^1$ represents hydrogen, hydroxyl or alkyl having 1 to 4 carbon atoms or cycloalkyl having 1 to 6 carbon atoms and
$A^2$ represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms, and phenyl, phenoxy, phenylthio, benzoyl, benzoylethenyl, cinnamoyl, heterocyclyl or phenylalkyl, phenylalkyloxy, phenylalkylthio, or heterocyclylalkyl having in each case 1 to 3 carbon atoms in the respective alkyl moieties, each of which is optionally mono- to trisubstituted in the ring moiety by halogen and/or straight-chain or branched alkyl or alkoxy having 1 to 4 carbon atoms.

Generally, $R^5$ represents in particular methyl or ethyl.
Generally, $R^6$ represents in particular hydrogen or methyl.
Generally, $R^7$ represents in particular methyl.
Generally, Q represents in particular oxygen or sulphur.
Generally, Y represents in particular fluorine, chlorine, bromine or iodine.
Generally, $T^1$ represents in particular fluorine or chlorine.
Generally, $T^2$ represents in particular fluorine or chlorine.
In general, $R^1$, $R^2$, $R^3$ and $R^4$ are identical or different and independently of one another each represents in particular hydrogen, halogen, cyano, nitro, or alkyl, alkoxy, alkylthio, alkylsulphinyl or alkylsulphonyl having in each case 1 to 6 carbon atoms and being in each case optionally substituted by 1 to 5 halogen atoms.

Preference is given to inventions in which Z represents cyclopentyl or cyclohexyl, each of which is optionally mono- to disubstituted by fluorine, chlorine, methyl, ethyl or hydroxyl;

represents optionally methyl- or ethyl-substituted thienyl, pyridyl or furyl;

or represents phenyl or naphthyl, each of which is optionally mono- to tetrasubstituted by identical or different substituents, where the possible substituents are preferably selected from the list below:

fluorine, chlorine, bromine, iodine, cyano, nitro, amino, hydroxyl, formyl, carboxyl, carbamoyl, thiocarbamoyl, methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl, methoxy, ethoxy, n- or i-propoxy, methylthio, ethylthio, n- or i-propylthio, methylsulphinyl, ethylsulphinyl, methylsulphonyl or ethylsulphonyl, vinyl, allyl, 2-methylallyl, propene-1-yl, crotonyl, propargyl, vinyloxy, allyloxy, 2-methylallyloxy, propene-1-yloxy, crotonyloxy, propargyloxy;

trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methylamino, ethylamino, n- or i-propylamino, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl, in each case doubly attached propanediyl, ethyleneoxy, methylenedioxy, ethylenedioxy, each of which is optionally mono- to tetrasubstituted by identical or different substituents from the group consisting of fluorine, chlorine, oxo, methyl and trifluoromethyl, or a grouping

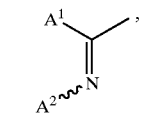

where
$A^1$ represents hydrogen, methyl or hydroxyl and
$A^2$ represents hydroxyl, methoxy, ethoxy, amino, methylamino, phenyl, benzyl or hydroxyethyl, and phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is optionally mono- to trisubstituted in the ring moiety by halogen and/or straight-chain or branched alkyl or alkoxy having 1 to 4 carbon atoms.

Preference is given to compounds in which $R^5$ represents methyl.

Preference is given to compounds in which $R^6$ represents hydrogen or in particular methyl.

Preference is given to compounds in which $R^7$ represents methyl.

Preference is given to compounds in which Q represents sulphur or in particular oxygen.

Preference is given to compounds in which Y represents fluorine or chlorine.

Preference is given to compounds in which $R^1$, $R^2$, $R^3$ and $R^4$ are identical or different and independently of one another each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

In a very particularly preferred group of compounds, Z represents optionally substituted phenyl.

In a further very particularly preferred group of compounds $R^1$ and $R^3$ independently of one another represent methyl and in particular hydrogen and $R^2$ and $R^4$ represent hydrogen.

Particular preference is given to compounds in which Y represents fluorine.

Particular preference is given to compounds in which Q represents oxygen.

The abovementioned general or preferred radical definitions apply both to the end products of the formula (I) and/or the formula (XI) and also correspondingly to the starting materials or intermediates required in each case for the preparation.

The radical definitions given in the respective combinations or preferred combinations of radicals for these individual radicals are, independently of the combination of radicals given in each case, also replaced by any radical definitions of other preferred ranges.

These radical definitions can be combined with each other at will, i.e. including combinations between the given ranges of preferred compounds.

The compound of the formula (XI-1, E-isomer) is novel and inventive and forms also part of the subject-matter of the invention. It can be used by way of example as pesticide.

(XI-1, E-isomer)

The compound of the formula (XI-1, Z-isomer) is novel and inventive and forms also part of the subject-matter of the invention. It can be used by way of example as pesticide.

(XI-1, Z-Isomer)

The isomerization of the compounds of the formula (XI) is preferably carried out after process steps 10 and 11.

Suitable diluents for carrying out the process according to the invention are, by way of example and by way of preference, alcohols, in particular methanol; ethers, in particular tetrahydrofuran; or alkylnitriles, in particular acetonitrile.

Preferred diluents for carrying out the process step 1 are ethers, in particular tetrahydrofuran; or alcohols, in particular ethanol, preferably methanol.

Preferred diluents for carrying out the process step 2 are alcohols, in particular methanol, pyridine, water or mixtures thereof.

Preferred diluents for carrying out process step 3 are alcohols, in particular methanol; dialkyl ketones, in particular acetone; dialkylformamides, in particular dimethylformamide, pyrrolidone, or dialkylacetamides; in particular dimethylacetamide.

Preferred diluents for carrying out the process step 4 are alkylnitriles, in particular acetonitrile.

Preferred diluents for carrying out the process step 5 are alcohols, in particular methanol, pyridine, water or mixtures thereof.

Preferred diluents for carrying out the process step 6 are alcohols, in particular methanol.

Preferred diluents for carrying out the process step 7 are alcohols, in particular methanol.

Preferred diluents for carrying out the process step 8 are alcohols, in particular methanol.

Preferred diluents for carrying out the process step 9 are alkylnitriles, in particular acetonitrile, dialkyl ketones, in particular acetone, dialkylformamides, in particular dimethylformamide, pyrrolidone, or dialkylacetamides, in particular dimethylacetamide.

Preferred diluents for carrying out the process step 10 are alkylnitriles, in particular acetonitrile, dialkyl ketones, in particular acetone, dialkylformamides, in particular dimethylformamide, pyrrolidone, or dialkylacetamides, in particular dimethylacetamide.

Preferred diluents for carrying out the process step 11 are alkylnitriles, in particular acetonitrile, dialkyl ketones, in particular acetone, dialkylformamides, in particular dimethylformamide, pyrrolidone, or dialkylacetamides, in particular dimethylacetamide.

Suitable diluents for carrying out the isomerization are all inert organic solvents. These preferably include aromatic hydrocarbons, such as for example toluene or xylene, esters, such as, for example, ethyl acetate or n-butylacetate, ethers, such as, for example tert-butyl methyl ether, dioxane, tetrahydrofuran or dimethoxyethane, ketones, such as, for example, acetone, butanone, cyclohexanone or methyl isobutylketone, or alcohols, such as, for example methanol, ethanol, n- or i-propanol, n-, i-, or t- butanol, or mixtures thereof with water.

For the purpose of the invention, acids are relatively highly concentrated acids, in particular mineral acids or hydrogen chloride gas.

The preferred mineral acid is hydrochloric acid, in particular hydrogen chloride gas.

For the isomerization, relatively highly concentrated acids, in particular mineral acids or sulfonic acids, for example and in particular sulfuric acid, methanesulfonic acid, hydrochloric acid and hydrogen chloride gas are employed.

The acidic ion exchangers used in the processes according to the invention are preferably perfluorinated ion exchangers.

The processes according to the invention are, if appropriate, carried out in the presence of a suitable acid acceptor/base. Suitable acid acceptors/bases are all customary inorganic or organic bases. These preferably include alkaline earth metal or alkali metal carbonates, such as, for example, potassium carbonate; alkaline earth metal or alkali metal bicarbonates, such as, for example, potassium bicarbonate; primary amines, such as methylanine, tertiary amines, such as trimethylamine, triethylamine, tributylamine, N,N-dimethylaniline, pyridine, N-methylpiperidine, N-methylmorpholine, N,N-dimethylaminopyridine, diazabicyclooctane (DABCO), diazabicyclononene (DBN) or diazabicycloundecene (DBU), particularly preferably alkali metal acetates, in particular sodium acetate.

In process step 1, preference is given to using methylamine.

In process step 3, preference is given to using sodium acetate.

In process step 4, preference is given to using potassium bicarbonate.

In process step 5, preference is given to using sodium acetate.

In process step 9, preference is given to using potassium carbonate.

In process step 10, preference is given to using potassium carbonate.

In process step 11, preference is given to using potassium carbonate.

The alkoxyamines used in process step 5 are in particular methoxyamine and/or its hydrochloride salt.

The alkoxyamines used in process step 6 are in particular methoxyamine and/or its hydrochloride salt.

When carrying out the processes according to the invention, the reaction temperatures can be varied within a relatively wide range. In general, the processes are carried out in a temperature range of from 0° C. to the reflux temperature of the mixture in question, in particular at reflux temperature.

The reactions according to process step 1 are preferably carried out in a temperature range from 0° C. to room temperature, in particular at 5–15° C.

The reactions according to process step 2 are preferably carried out in a temperature range from room temperature to the reflux temperature of the mixture in question, in particular at reflux temperature.

The reactions according to process step 3 are preferably carried out in a temperature range from room temperature to the reflux temperature of the mixture in question, in particular at room temperature.

The reactions according to process step 4 are preferably carried out in a temperature range from room temperature to the reflux temperature of the mixture in question, in particular at reflux temperature.

The reactions according to process step 5 are preferably carried out in a temperature range from room temperature to the reflux temperature of the mixture in question, in particular at reflux temperature.

The reactions according to process step 6 are preferably carried out in a temperature range from room temperature to the reflux temperature of the mixture in question, in particular at reflux temperature.

The reactions according to process step 7 are preferably carried out in a temperature range from room temperature to the reflux temperature of the mixture in question.

The reactions according to process step 8 are preferably carried out in a temperature range from room temperature to the reflux temperature of the mixture in question.

The reactions according to process step 9 are preferably carried out in a temperature range from room temperature to the reflux temperature of the mixture in question.

The reactions according to process step 10 are preferably carried out in a temperature range from room temperature to the reflux temperature of the mixture in question.

The reactions according to process step 11 are preferably carried out in a temperature range from room temperature to the reflux temperature of the mixture in question.

The reactions of the processes according to the invention are carried out under atmospheric pressure, under elevated or under reduced pressure, preferably under atmospheric pressure.

Preferred carbonyl compounds are dialkyl ketones, in particular acetone, aldehydes or glyoxylic acid.

Preferred alkylating agents are carbonates, in particular dialkyl carbonates, particularly preferably dimethyl carbonate, dialkyl sulphates, in particular dimethyl sulphate, or particularly preferably alkyl halides, in particular methyl chloride.

Preferred pyrimidine derivatives of the formula (XII) in process step 9) are trifluoropyrimidine or fluorodichloropyrimidines, in particular 5-fluoro-4,6-dichloropyrimidine.

Particular preference is given to carrying out process part 1A)a) without intermediate isolation of the compounds of the formulae (VI), (VII) and (II) (one-pot process).

Particular preference is given to carrying out process part 1A)b) without intermediate isolation of the compounds of the formulae (VI) and (II) (one-pot process).

Particular preference is given to carrying out process part 1B) without intermediate isolation of the compounds of the formula (II) (one-pot process)

Particular preference is given to carrying out process part 1C) without intermediate isolation of the compounds of the formula (VII) and (II) (one-pot process).

Particular preference is given to carrying out process part 1D) without intermediate isolation of the compounds of formula (II) (one-pot process).

Particular preference is given to carrying out process part 1 and part 2 without isolation of the intermediate compounds (one-pot process).

The starting materials of the formula (IV) used for carrying out the process steps 2), 6) and 7) are known and can be prepared by known processes (cf. Beilstein, E (II) 17, 462; Mameli, G. 56, 768; Chem. Ber. 35 (1902), 1640–1646; Proc. Indian Acad. Sci. Sect. A (1976) 83A(6), 238–242).

Some of the compounds of the formula (VII) required as starting materials for carrying out the process step 4) according to the invention are known (cf. Giannella; Pigini, FRPSAX, Farmaco Ed.Sci., 28, 1973, 157,159), and they are obtained by a novel route according to process step 7) from compounds of the formula (IV), or according to process step 3) from compounds of the formula (VI).

On the one hand, the compounds of the formula (VI) required as starting materials for carrying out the known process step 5) are known and can be prepared by processes known per se, on the other hand, they are obtained by a novel route according to process step 2).

The compounds of the formula (IV) required as starting materials for carrying out the process step 3) according to the invention have already been described in the description of the process step 5).

The starting materials of the formula (X) used in process step 8) in which $R^1$, $R^2$, $R^3$ and $R^4$ represent hydrogen and $R^5$ represents methyl are mentioned by name in EP-398692, the starting materials of the formula (X), used in process step 8) in which $R^1$, $R^2$, $R^3$ and $R^4$ represent hydrogen and $R^5$ represents alkyl are described under formula (VIII) on page 8 and page 14 and page 36 in WO9746542. They are also described under formula (IV) on page 7 and 8 and on pages 17, 19 and 20 in EP-846691.

The starting materials of the formula (II) used for carrying out the process step 1) can be prepared by process part 1Aa), process part 1Ab), process part 1B, process part 1C or by process part 1D by carrying out the process steps successively or by a one-pot process.

The starting materials used for carrying out the process steps 9), 10) and 11) are described in WO 98/21189.

The compounds of the formula (XI) used for carrying out the isomerization are obtained according to process part 1 and part 2.

All other starting materials are customary commercial products or can be prepared from these by simple processes.

Process step 2 is novel and also forms part of the subject-matter of the invention.

The process step 3) according to the invention yields the compounds of the formula (VII). The compounds of the formula (VII) are novel and inventive and form part of the subject-matter of the invention, except for the compounds of the formula (VII-a)

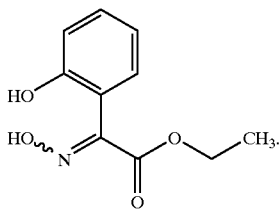

(VII-a)

The process step 7) according to the invention yields the compounds of the formula (VII). The compounds of the formula (VII) are novel and inventive and form part of the subject-matter of the invention.

With the aid of the entire process (process part 1 and process part 2), the preparation of the known pesticides of the formula (XI) (cf. WO 98/21189) is considerably improved and simplified.

The process part 1 according to the invention serves to prepare important intermediates of the formula (I) and gives these intermediates a high and improved yield.

In process part 2 according to the invention, too, an increased yield in comparison to known processes can be observed.

By carrying out the isomerization after process part 2, in particular after process steps 10 and 11, the proportion of the E isomer in the isomer mixture is increased.

The examples below serve to illustrate the invention. The invention is, however, not limited to the examples.

EXAMPLES

I. Process Part 1)
Process Part 1 A a) (Process Steps 2, 3, 4 and 1)

Process Step 2

Methyl 2-Hydroxyphenylglyoxylate (Example VI-1a)

6.38 g of acetyl chloride (0.081 mol) are added dropwise to a mixture of 65 ml of methanol and 65 ml of acetone. 5.2 g (0.032 mol) of benzofuran-2,3-dione 2-oxime are dissolved in this mixture, and the mixture is subsequently heated under reflux for 1 hour. The solvent is distilled off under reduced pressure, the residue is poured into water, the product is extracted with diethyl ether, the organic phase is dried over sodium sulphate and the solvent is distilled off under reduced pressure. This gives 5.2 g of crude product which is chromatographed over silica gel using a mixture of 7 parts n-hexane and 3 parts acetone. This gives 3.8 g of a product which, according to HPLC, contains 88% of methyl 2-hydroxyphenylglyoxylate of log p=1.87.

Process Step 3

Methyl 2-(2-Hydroxyphenyl)-2-hydroxyimino-acetate (Example VII-1a)

3.3 g (0.016 mol) of methyl 2-hydroxyphenylglyoxylate (HPLC: 88%, log p=1.87) (Example VI-1a) and 1.3 g (0.019 mol) of hydroxylamine hydrochloride in 50 ml of methanol are heated under reflux for one hour. The reaction mixture is poured into water, acidified with 2N hydrochloric acid and extracted with diethyl ether, the organic phase is dried over sodium sulphate and the solvent is distilled off under reduced pressure. This gives 2.4 g of crude product which, according to HPLC, contains 17.1% of methyl E-2-(2-hydroxyphenyl)-2-hydroxyimino-acetate of log p=0.95 and 68.9% of methyl Z-2-(2-hydroxyphenyl)-2-hydroxyimino-acetate of log p=1.68.

Process Step 4

Methyl 2-(2-Hydroxyphenyl)-2-methoxyimino-acetate (Example II-1a)

2.4 g (0.0106 mol) of methyl 2-(2-hydroxyphenyl)-2-hydroxyimino-acetate (Example VII-1a from process step 3; HPLC: 17.1% E, log p=0.95; 68.9% Z, log p=1.68) in 60 ml of acetonitrile are heated under reflux with 1.08 g (0.011 mol) of potassiun bicarbonate and 1.55 g (0.0123 mol) of dimethyl sulphate for 10 hours. The reaction mixture is poured into water and extracted with diethyl ether, and the solvent is distilled off under reduced pressure. This gives 2.1 g of crude product which is chromatographed over silica gel using a mixture of 7 parts of n-hexane and 3 parts of acetone. This gives 1.6 g of product which, according to HPLC, contains 36.9% of methyl Z-2-(2-hydroxyphenyl)-2-methoxyimino-acetate of log p=2.39.

Process Part 1 A b) (Process Steps 2, 5 and 1)

Process Step 2

Methyl 2-Hydroxyphenylglyoxylate (Example VI-1)

27 g of acetyl chloride (0.344 mol) are added dropwise to a mixture of 245 ml of methanol and 245 ml of acetone. 20 g (0.123 mol) of benzofuran-2,3-dione 2-oxime are dissolved in this mixture and the mixture is subsequently heated under reflux for 1 hour. The solvent is distilled off under reduced pressure, the residue is poured into water, the product is extracted with diethyl ether, the organic phase is dried over sodium sulphate and the solvent is distilled off under reduced pressure. This gives 20.8 g of crude product which, according to HPLC, contains 92.4% methyl 2-hydroxyphenylglyoxylate of log p=1.87.

Process Step 5

Methyl 2-(2-Hydroxyphenyl)-2-methoxyimino-acetate (Example II-1b)

10.4 g (0.0533 mol) of methyl 2-hydroxyphenylglyoxylate (HPLC: 92.4%, log p=1.87) from process step 2 and 7.4 g (0.089 mol) of 0-methylhydroxylamine hydrochloride in 150 ml of methanol are boiled under reflux for three hours. The reaction mixture is poured into water, the product is extracted with diethyl ether, the organic phase is dried over sodium sulphate and the solvent is distilled off under reduced pressure. This gives 8.2 g of crude product which, according to HPLC, contains 17.2% methyl E-2-(2-hydroxyphenyl)-2-methoxyimino-acetate of log p=1.48 and 65.4% methyl Z-2-(2-hydroxyphenyl)-2-methoxyimino-acetate of log p=2.38.
Process Part 1 B) (Process Steps 6 and 1)

Process Step 6

Methyl 2-(2-Hydroxyphenyl)-2-methoxyimino-acetate (Example II-1c)

8.2 g (0.05 mol) of benzofuran-2,3-dione 2-oxime and 9 g (0.108 mol) of O-methylhydroxylamine hydrochloride in 50 ml of methanol are heated under reflux for 3 hours. The methanol is distilled off under reduced pressure and the residue is mixed with 50 ml of water and extracted with ethyl acetate. The organic phase is dried over sodium sulphate and the solvent is distilled off under reduced pressure, giving 9.88 g of crystal-containing crude product. According to HPLC, the crude product contains 43.7% of methyl E-2-(2-hydroxyphenyl)-2-methoxyimino-acetate of log p=1.48 and 29.4% of methyl Z-2-(2-hydroxyphenyl)-2-methoxyimino-acetate of log p=2.37.

$^1$H-NMR spectrum (DMSO-d$_6$/TMS): E isomer: 3.72 ppm (3H, s); 3.92 ppm (3H, s); Z isomer: 3.77 ppm (3H, s); 3.92 ppm (3H, s).
Process Part 1 C) (Process Steps 7, 4 and 1)

Process Step 7

Methyl 2-(2-Hydroxyphenyl)-2-hydroxyimino-acetate (Example VII-1d)

4.9 g of acetyl chloride (0.062 mol) are added dropwise to 100 ml of methanol. 4.0 g (0.0245 mol) of benzofuran-2,3-dione 2-oxime are dissolved in this mixture, and the mixture is then heated under reflux for 12 hours. The solvent is distilled off under reduced pressure, the residue is poured into water, the product is extracted with diethyl ether, the organic phase is dried over sodium sulphate and the solvent is distilled off under reduced pressure. This gives 3.9 g of crude product which, according to HPLC, contains 21.7% of methyl E-2-(2-hydroxyphenyl)-2-hydroxyimino-acetate of log p=0.95 and 56% of methyl Z-2-(2-hydroxyphenyl)-2-hydroxyimino-acetate of log p=1.68.

GC/MS silylated:
E isomer: 22.0%, retention index=1673, M=339, 324, 308, 280, 250, 220, 206, 176, 147, 131, 89,73, 59, 45.
Z isomer: 60.5%, retention index=1744, M=339, 324, 296, 280, 220, 250, 206, 176, 147, 131, 89, 73, 59, 45.
This crude product is chromatographed over silica gel using a mixture of 7 parts of n-hexane and 3 parts of acetone. This gives 2.3 g of a product which, according to HPLC, contains 86.4% of methyl Z-2-(2-hydroxyphenyl)-2-hydroxyimino-acetate of log p=1.70 and 11.8% E-benzofuran-2,3-dione 3-oxime of log p=1.55.

Process Step 4

Methyl 2-(2-Hydroxyphenyl)-2-methoxyimino-acetate (Example II-1d)

1.7 g (0.0075 mol) of methyl 2-(2-hydroxyphenyl)-2-hydroxyimino-acetate (HPLC: 86.4% Z, log p=1.70) (Example VII-1d from process step 7) in 40 ml of acetonitrile are heated under reflux with 0.77 g (0.0076 mmol) of potassium bicarbonate and 1.1 g (0.0087 mol) of dimethyl sulphate for 10 hours. The reaction mixture is poured into water, the product is extracted with diethyl ether and the solvent is distilled off under reduced pressure. This gives 1.2 g of crude product which, according to HPLC, contains 46% of methyl Z-2-(2-hydroxyphenyl)-2-methoxyimino-acetate of log p=2.38. This crude product is chromatographed over silica gel using a mixture of 7 parts of n-hexane and 3 parts of acetone. This gives 0.8 g of a product which, according to HPLC, contains 54.4% methyl Z-2-(2-hydroxyphenyl)-2-methoxyimino-acetate of log p=2.39.
Process Part 1 D) (Process Steps 8 and 1)

Process Step 8

Methyl 2-(2-Hydroxyphenyl)-2-methoxyimino-acetate (Example II-1e)

5 g of acetyl chloride (0.064 mol) are added dropwise to 50 ml of methanol. 4.8 g (0.025 mol) of benzofuran-2,3-dione 3-(O-methyl-oxime) 2-oxime are dissolved in this mixture, and the reaction mixture is then heated under reflux for 12 hours. After cooling to room temperature, the mixture is poured into water and the product is extracted with diethyl ether. The organic phase is washed with aqueous sodium bicarbonate solution and dried over sodium sulphate, and the solvent is distilled off under reduced pressure. This gives 4.33 g of crude product which, according to HPLC, contains 27.4% methyl E-2-(2-hydroxyphenyl)-2-methoxyimino-acetate of log p=1.48 and 56% methyl Z-2-(2-hydroxyphenyl)-2-methoxyimino-acetate of log p=2.37.

$^1$H-NMR spectrum (DMSO-d$_6$/TMS): E isomer: 3.72 ppm (3H, s); 3.92 ppm (3H, s); Z isomer: 3.77 ppm (3H, s) and 3.92 ppm (3H, s).
Process Part 1 D) (Process Steps 8 and 1, One-pot Synthesis)

N-Methyl-2-(2-hydroxyphenyl)-2-methoxyimino-acetamide (Example I-1f)

5 g of acetyl chloride (0.064 mol) are added dropwise to 50 ml of methanol. 4.8 g (0.025 mol) of benzofuran-2,3-dione 3-(O-methyl-oxime) 2-oxime are dissolved in this mixture, and the reaction mixture is then heated under reflux for 12 hours. The mixture is subsequently cooled to 0° C., methylamine is introduced until saturation has been reached and the reaction mixture is allowed to stand at 10° C. for 12 hours. The solvent is distilled off under reduced pressure and the residue is admixed with a mixture of 15 ml of 2N hydrochloric acid and 15 ml of saturated sodium chloride solution and extracted three times with 25 ml of ethyl acetate each time. The organic phase is dried over sodium sulphate and the solvent is distilled off under reduced pressure. This gives 6.2 g of crude product which, according to HPLC, contains 37.9% N-methyl-E-2-(2-hydroxyphenyl)-2-methoxyimino-acetamide of log p=0.98 and 44% N-methyl-Z-2-(2-hydroxyphenyl)-2-methoxyiminoacetamide of log p1.29.

$^1$H-NMR spectrum (DMSO-d$_6$/TMS): E isomer: 2.67/2.68 ppm (3H, d); 3.86 ppm (3H, s); Z isomer: 2.73/2.75 ppm (3H, d); 3.93 ppm (3H, s).

Process Part 1 D) (Process Steps 8 and 1: Addition of Acetone as Carbonyl Compound in Process Step 8)

Process Step 8

Methyl 2-(2-Hydroxyphenyl)-2-methoxyimino-acetate (Example II-1g)

10.5 g of acetyl chloride (0.133 mol) are added dropwise to a mixture of 100 ml of methanol and 100 ml of acetone. 10 g (0.052 mol) of benzofuran-2,3-dione 3-(O-methyl-oxime) 2-oxime are dissolved in this mixture, and the reaction mixture is then stirred at room temperature for 12 hours. The mixture is poured into water and the product is extracted with ethyl acetate. The organic phase is washed with aqueous sodium bicarbonate solution and dried over sodium sulphate, and the solvent is distilled off under reduced pressure. This gives 9 g of crude product which, according to HPLC, contains 17.7% methyl E-2-(2-hydroxyphenyl)-2-methoxyimino-acetate of log p=1.48 and 61.8% methyl Z-2-(2-hydroxyphenyl)-2-methoxyimino-acetate of log p=2.38.

$^1$H-NMR spectrum (DMSO-d$_6$/TMS): E isomer: 3.72 ppm (3H, s); 3.92 ppm (3H, s); Z isomer: 3.77 ppm (3H, s); 3.91 ppm (3H, s).

Process Step 1)

a) N-Methyl-2-(2-hydroxyphenyl)-2-methoxyimino-acetamide (Example I-1a)

1.2 g (0.0021 mol) of methyl 2-(2-hydroxyphenyl)-2-methoxyimino-acetate (in particular Example II-1a from process step 4; HPLC: 36.9% methyl Z-2-(2-hydroxyphenyl)-2-methoxyimino-acetate of log p=2.39) are dissolved in 14 ml of tetrahydrofuran and cooled to 10° C. With cooling, methylamine is introduced. After about 30 minutes, 5 ml of methanol are added, the solution is saturated with methylamine and the mixture is allowed to stand at 10° C. overnight. The solvents are distilled off under reduced pressure and the residue is admixed with a mixture of 10 ml of 2N hydrochloric acid and 10 ml of saturated sodium chloride solution and extracted three times with 20 ml of ethyl acetate in each case. The organic phase is dried over sodium sulphate and the solvent is distilled off under reduced pressure, giving 1.3 g of crude product. The crude product is chromatographed over silica gel using a mixture of 7 parts of n-hexane and 3 parts of acetone.

This gives 0.7 g of product which, according to HPLC, contains 37.9% of N-methyl-Z-2-(2-hydroxyphenyl)-2-methoxyiminoacetamide of log p=1.32.

b) N-Methyl-2-(2-hydroxyphenyl)-2-methoxyimino-acetamide (Example I-1b)

8 g (0.0316 mol) of crude product (methyl E/Z-2-(2-hydroxyphenyl)-2-methoxyimino-acetate, in particular Example II-1b from process step 5; HPLC: 17.2% methyl E-2-(2-hydroxyphenyl)-2-methoxyimino-acetate of log p=1.48 and 65.4% methyl Z-2-(2-hydroxyphenyl)-2-methoxyimino-acetate of log p=2.38) are dissolved in 100 ml of tetrahydrofuran and cooled to 10° C. With cooling, methylamine is introduced. After about 30 minutes, 30 ml of methanol are added, the solution is saturated with methylamine and the mixture is allowed to stand at 10° C. overnight. The solvent is distilled off under reduced pressure and the residue is admixed with a mixture of 15 ml of 2N hydrochloric acid and 15 ml of saturated sodium chloride solution and extracted three times with 25 ml of ethyl acetate each time. The organic phase is dried over sodium sulphate and the solvent is distilled off under reduced pressure, giving 8.1 g of crude product which, according to HPLC, contains 40.3% of N-methyl-E-2-(2-hydroxyphenyl)-2-methoxyimino-acetamide of log p=0.98 and 53.1% of N-methyl-Z-2-(2-hydroxyphenyl)-2-methoxy-iminoacetamide of log p=1.29.

c) Methyl-2-(2-hydroxyphenyl)-2-methoxyimino-acetamide (Example I-1c)

Methyl E/Z-2-(2-hydroxyphenyl)-2-methoxyimino-acetate, in particular the crude mixture obtained according to process step 6, is further reacted analogously to the procedure described in EP-398692 (cf. Example 30, page 49, Preparation of the E isomer and the Z isomer from N-methyl-(2-(2-hydroxy)phenyl)-2-methoxyiminoacetamide from the methyl E,Z-2-(2-hydroxyphenyl)-2-methoxyimino-acetate mixture which is present in situ) as follows:

9.68 g of crude product (0.0339 mol of methyl E/Z-2-(2-hydroxyphenyl)-2-methoxyimino-acetate, in particular compound II-1c from process step 6, HPLC: 43.7% E isomer of log p=1.48; 29.4% Z isomer of log p=2.37) are dissolved in 100 ml of tetrahydrofuran and cooled to 10° C. With cooling, methylamine is introduced. After about 30 minutes, 50 ml of methanol are added, the solution is saturated with methylamine and the mixture is allowed to stand at 10° C. overnight. The solvents are distilled off under reduced pressure and the residue is mixed with a mixture of 30 ml of 2N hydrochloric acid and 30 ml of saturated sodium chloride solution and extracted three times with 50 ml of ethyl acetate each time. The organic phase is dried over sodium sulphate and the solvent is distilled off under reduced pressure, giving 8.5 g of crude product which, according to HPLC, contains 52.6% N-methyl-E-2-(2-hydroxyphenyl)-2-methoxyimino-acetamide of log p=0.98 and 31.9% N-methyl-Z-2-(2-hydroxyphenyl)-2-methoxyiminoacetamide of log p=1.29.

$^1$H-NMR spectrum (DMSO-d$_6$/TMS): E isomer: 2.67/2.68 ppm (3H, d); 3.86 ppm (3H, s); Z isomer: 2.73/2.75 ppm (3H, d); 3.93 ppm (3H, s).

d) N-Methyl-2-(2-hydroxyphenyl)-2-methoxyimino-acetamide (Example I-1d)

0.5 g (0.0013 mol) of methyl 2-(2-hydroxyphenyl)-2-methoxyimino-acetate (in particular Example II-Id from process step 4; HPLC: 54.4% methyl Z-2-(2-hydroxyphenyl)-2-methoxyimino-acetate of log p=2.39 is disolved in 6 ml of tetrahydrofuran and cooled to 10° C. With cooling, methylamine is introduced. After about 30 minutes, 2 ml of methanol are added, the solution is saturated with methylamine and the mixture is allowed to stand at 10° C. overnight. The solvents are distilled off under reduced pressure and the residue is mixed with a mixture of e) N-Methyl-2-(2-hydroxyphenyl)-2-methoxyimino-acetamide (Example I-1e)

4.33 g (0.0173 mol) of crude product methyl E/Z-2-(2-hydroxyphenyl)-2-methoxyimino-acetate, in particular Example II-1e from process step 8; HPLC: 27.4% methyl E-2-(2-hydroxyphenyl)-2-methoxyimino-acetate of log p=1.48 and 56% methyl Z-2-(2-hydroxyphenyl)-2-methoxyimino-acetate of log p=2.38) are dissolved in 50 ml of tetrahydrofuran and cooled to 10° C. With cooling, methylamine is introduced. After about 30 minutes, 15 ml of methanol are added, the solution is saturated with methylamine and the mixture is allowed to stand at 10° C. overnight. The solvents are distilled off under reduced pressure and the residue is mixed with a mixture of 15 ml of 2N hydrochloric acid and 15 ml of saturated sodium chloride solution and extracted three times with 25 ml of ethyl acetate each time. The organic phase is dried over sodium sulphate and the solvent is distilled off under reduced pressure, giving 4.3 g of crude product which, according to HPLC, contains 38.8% N-methyl-E-2-(2-hydroxyphenyl)-2-methoxyimino-acetamide of log p=0.98 and 51% N-methyl-Z-2-(2-hydroxyphenyl)-2-methoxyiminoacetamide of log p=1.29.

[1] H-NMR spectrum (DMSO-$d_6$/TMS): E isomer: 2.66/2.68 ppm (3H, d); 3.86 ppm (3H, s); Z isomer: 2.73/2.75 ppm (3H, d); 3.93 ppm (3H, s).

f) N-Methyl-2-(2-hydroxyphenyl)-2-methoxyimino-acetamide (Example I-1g)

9 g (0.0342 mol) of crude product methyl E/Z-2-(2-hydroxyphenyl)-2-methoxyimino-acetate, in particular Example II-1g from process step 8; HPLC; 17.7% methyl E-2-(2-hydroxyphenyl)-2-methoxyimino-acetate of log p=1.48 and 61.8% methyl Z-2-(2-hydroxyphenyl)-2-methoxyimino-acetate of log p=2.38) are dissolved in 100 ml of tetrahydrofuran and cooled to 10° C. With cooling, methylamine is introduced. After about 30 minutes, 20 ml of methanol are added, the solution is saturated with methylamine and the mixture is allowed to stand at 10° C. overnight. The solvents are distilled off under reduced pressure and the residue is admixed with a mixture of 30 ml of 2N hydrochloric acid and 30 ml of saturated sodium chloride solution and extracted three times with 75 ml of ethyl acetate each time. The organic phase is dried over sodium sulphate and the solvent is distilled off under reduced pressure, giving 6 g of crude product which, according to HPLC, contains 43.7% of N-methyl-E-2-(2-hydroxyphenyl)-2-methoxyimino-acetamide of log p=0.98 and 53.5% N-methyl-Z-2-(2-hydroxyphenyl)-2-methoxyiminoacetamide of log p=1.29.

II. Process Part 2

Process Part 2 E) (Process part 1 and Process Steps 9 and 10) Using the Compound (I-1g) Obtained in Process Step 8 According to Process Part 1 D) With Addition of Acetone as Carbonyl Compound Process Step 9

N-Methyl-2-[2-(5,6-difluoro-pyrimidin-4-yloxy)-phenyl]-2-methoxyiminoacetamide (Example XIII-1g) (cf. Example (IV-1) From WO9821189, Page 25)

6 g (0.0280 mol) of N-methyl-2-(2-hydroxyphenyl)-2-methoxyiminoacetamide (Example I-1g from process step 1; HPLC: 43.7% N-methyl-E-2-(2-hydroxyphenyl)-2-methoxyimino-acetamide of log p=0.98 and 53.5% N-methyl-Z-2-(2-hydroxyphenyl)-2-methoxyiminoacetamide of log p=1.29) are dissolved in 80 ml of acetonitrile. The solution is cooled to 0° C., 4.7 g (0.034 mol) of potassium carbonate are added and the mixture is stirred for another 30 minutes. 3.8 g (0.0283 mol) of 4,5,6-trifluoropyrimidine are then added dropwise and the mixture is stirred at 20° C. for two hours. The solvent is then distilled off under reduced pressure, the residue is mixed with water, the product is extracted with ethyl acetate, the organic phase is dried over sodium sulphate and the solvent is distilled off under reduced pressure. This gives 5.7 g (61.4% of theory) of crude N-methyl-2-[2-(5,6-difluoropyrimidin-4-yloxy)phenyl]-2-methoxyiminoacetamide which, according to HPLC, contains 45.5% N-methyl-E-2-[2-(5,6-difluoropyrimidin-4-yloxy)-phenyl]-2-methoxyiminoacetamide of log p=1.95 and 46.6% N-methyl-Z-2-[2-(5,6-difluoro-pyrimidin-4-yloxy)phenyl]-2-methoxyiminoacetamide of log p=1.87.

[1] H-NMR spectrum (CDCl$_3$/TMS): E isomer: 3.81 ppm (3H, s); 6.67 ppm (1H, b); Z isomer: 3.89 ppm (3H, s); 6.40 ppm (1H, b).

Process Step 10

N-Methyl-2-[2-(5-fluoro-2'-methyl-3'-chlorophenoxy-pyrimidin-4-yloxy)-phenyl]-2-methoxyiminoacetamide (Example XI-2g) Compounds (XI-1, E-Isomer and XI-1, Z-Isomer)

2.5 g (0.0175 mol) of 2-methyl-3-chlorophenol are dissolved in 20 ml of acetontrile. 4.5 g (0.0326 mol) of potassium carbonate are added and the mixture is stirred at room temperature for 30 minutes. The mixture is then cooled to 0° C. and 5.7 g (0.0163 mol) of N-methyl-2-[2-(5,6-difluoropyrimidin-4-yloxy)phenyl]-2-methoxyiminoacetamide (compound XIII-1g from process step 9, content by HPLC: 45.5% E isomer, 46.6% Z isomer) dissolved in acetonitrile are added dropwise. The mixture is stirred for 12 hours, during which the temperature is allowed to rise to room temperature. The solids are filtered off, the solvent is concentrated under reduced pressure and the residue is mixed with water and extracted with ethyl acetate. The solvent is distilled off under reduced pressure. This gives 2.9 g of product which, according to HPLC, contains 57.8% N-methyl-E-2-[2-(5-fluoro-2'-methyl-3'-chlorophenoxypyrimidin-4-yloxy)phenyl]-2-methoxyiminoacetamide (XI-1, E-isomer) of log p=3.51 and 30% N-methyl-Z-2-[2-(5-fluoro-2'-methyl-3'-chlorophenoxy-pyrimidin-4-yloxy)phenyl]-2-methoxyiminoacetamide (XI-1, Z-isomer) of log p=3.44.

Process Part 2 F) (Process 1 and Process Step 11)

Process Step 11

1. N-Methyl-2-[2-(5-fluoro-2'-chlorophenoxypyrimidin-4-yloxy)phenyl]-2-methoxyiminoacetamide (Example XI-1c, in Particular Using the Compound I-1c Obtained According to Process Part 1 B) Compounds (XI-2, E-Isomer and XI-2, Z-Isomer)

8.36 g (0.0339 mol) of crude N-methyl-E/Z-2-(2-hydroxyphenyl)-2-methoxyimino-acetamide mixture (I-1c)

(content by HPLC: E isomer: 52.6%, log p=0.98; Z isomer: 31.9%, log p=1.23) which had been obtained according to process 1 B) are dissolved in 50 ml of acetonitrile and, after addition of 6.7 g (0.048 mol) of potassium carbonate, the mixture is stirred at room temperature for one hour. 8 g (0.033 mol) of 4-(2'-chlorophenoxy)-5,6-difluoropyrimidine are added to the reaction mixture, and the mixture is stirred at room temperature for 16 hours. A further 1.8 g (0.0074 mol) of 4-(2'-chlorophenoxy)-5,6-difluoropyrimidine are then added dropwise, and the mixture is subsequently heated under reflux for 3 hours. The salts are filtered off, the solvent is distilled off under reduced pressure and the residue is partitioned between ethyl acetate and aqueous sodium carbonate solution. The organic phase is dried over sodium sulphate and the solvent is distilled off under reduced pressure. This gives 15.3 g of crude product which, according to HPLC, contains 21% N-methyl-Z-2-[2-(5-fluoro-2'-chlorophenoxypyrimidin-4-yloxy)-phenyl]-2-methoxyiminoacetamide (XI-2, Z-isomer) of log p=2.95 and 54.6% N-methyl-E-2-[2-(5-fluoro-2'-chlorophenoxypyrimidin-4-yloxy)phenyl]-2-methoxyiminoacetamide (XI-2, E-isomer) of log p=3.01.

2. N-Methyl-2-[2-(5-fluoro-2'-chlorophenoxypyrimidin-4-yloxy)phenyl]-2-methoxyimino-acetamide (Example XI-1e, in Particular Using the Compound I-1e obtained According to process Part 1 D)) Compounds (XI-2, E-Isomer and XI-2, Z-Isomer)

4.3 g (0.0185 mol) of crude N-methyl-E/Z-2-(2-hydroxyphenyl)-2-methoxyiminoacetamide mixture (in particular Example I-1e; HPLC: 56% E, log p=1.48; 27.4% Z, log p=2.38) from process 1 D) are dissolved in 100 ml of acetonitrile and, after addition of 3.1 g (0.022 mol) of potassium carbonate, stirred at room temperature for 30 minutes. 5 g (0.021 mol) of 4-(2'-chlorophenoxy)-5,6-difluoropyrimidine are added dropwise to the reaction mixture, and the mixture is stirred at room temperature for 12 hours. The mixture is then boiled at reflux for 3 hours. The mixture is poured into water and extracted 3 times with 100 ml of diethyl ether, the organic phase is dried and the solvent is distilled off under reduced pressure. This gives 7.8 g of crude product which, according to HPLC, contains 43.9% N-methyl-Z-2-[2-(5-fluoro-2'-chlorophenoxypyrimidin-4-yloxy)phenyl]-2-methoxyiminoacetamide (XI-2, Z-isomer) of log p=2.95 and 38.2% N-methyl-E-2-[2-(5-fluoro-2'-chlorophenoxypyrimidin-4-yloxy)phenyl]-2-methoxyiminoacetamide(XI-2, E-isomer) of log p=3.01.

7.8 g of crude N-methyl-2-[2-(5-fluoro-2'-chlorophenoxypyrimidin-4-yloxy)-phenyl]-2-methoxyiminoacetamide (XI-2, Z- and E-isomer) are dissolved in 50 ml of diethyl ether. With cooling, the solution is saturated with hydrogen chloride, the reaction mixture is allowed to stand at room temperature for 2 days. The solvent is distilled off under reduced pressure, the residue is taken up in ethyl acetate and the mixture is washed with water. The organic phase is dried over sodium sulphate and the solvent is distilled off under reduced pressure. The residue is triturated with diethyl ether and filtered off, giving 5 g of crystals which, according to HPLC, 5 contain 97.28% N-methyl-E-2-[2-(5-fluoro-2'-chlorophenoxypyrimidin-4-yloxy)phenyl]-2-methoxyiminoacetamide (XI-2, E-isomer) of log p=3.01 and 2.94% N-methyl-Z-2-[2-(5-fluoro-2'-chlorophenoxypyrimidin-4-yloxy)phenyl]-2-methoxyiminoacetamide (XI-2, E-isomer) of log p=2.95.

3. N-Methyl-2-[2-(5-fluoro-2'-methyl-3'-chlorophenoxypyrimidin-4-yloxy)-phenyl]-2-methoxyiminoacetamide (Example XI-2f, Using the Compound I-1f Obtained According to Process Part 1 D) (One-pot Synthesis)) Compounds (XI-1, E-Isomer and XI-1, Z-Isomer)

6 g (0.0236 mol) of crude N-methyl-E/Z-2-(2-hydroxyphenyl)-2-methoxyimino-acetamide mixture (in particular Example I-1f; HPLC: 37.9% E, log p=0.98; 44% Z, log p=1.29) are dissolved in 100 ml of acetonitrile and, after addition of 3.5 g (0.025 mol) of potassium carbonate, stirred at room temperature for 30 minutes. 6 g (0.0234 mol) of 4-(2'-methyl-3'-chlorophenoxy)-5,6-difluoropyrimidine are added dropwise to the reaction mixture, and the mixture is stirred at room temperature for 12 hours. The mixture is then heated under reflux for 3 hours. The mixture is poured into water and extracted 3 times with 100 ml of ethyl acetate, and the organic phase is dried over sodium sulphate. The organic phase is saturated with hydrogen chloride and the solution is allowed to stand at room temperature for 24 hours. The solvent is subsequently distilled off under reduced pressure, the residue is taken up in ethyl acetate, the organic phase is washed with water and dried over sodium sulphate and the solvent is distilled off under reduced pressure, giving 8.4 g of product.

According to HPLC, the product contains 9.4% N-methyl-Z-2-[2-(5-fluoro-2'-methyl-3'-chlorophenoxypyrimidin-4-yloxy)phenyl]-2-methoxyiminoacetamide (XI-1, Z-isomer) of log p=3.43 and 63.8% N-methyl-E-2-[2-(5-fluoro-2'-methyl-3'-chlorophenoxy-pyrimidin-4-yloxy)phenyl]-2-methoxyiminoacetamide (XI-1, E-isomer) of log p=3.50.

This product is triturated with diethyl ether and filtered off. This gives 4 g of crystals which, according to HPLC, contain 90.5% N-methyl-E-2-[2-(5-fluoro-2'-methyl-3'-chlorophenoxypyrimidin-4-yloxy)phenyl]-2-methoxyiminoacetamide (XI-1, E-isomer) of log p=3.50 and 4.6% N-methyl-Z-2-[2-(5-fluoro-2'-methyl-3'-chlorophenoxypyrimidin-4-yloxy)-phenyl]-2-methoxyiminoacetamide (XI- 1, Z-isomer) of log p=3.43. The mother liquor is concentrated under reduced pressure, giving 3.9 g of a mixture containing 30.2% E-product (XI-1, E-isomer) of log p=3.50 and 13% Z-product (XI-1, Z-isomer) of log p=3.43.

4. N-Methyl-2-[2-(5-fluoro-2'-chlorophenoxypyrimidin-4-yloxy)phenyl]-2-methoxyiminoacetamide (Example XI-1f, Using the Compound I-1f Obtained According to Process Part 1 D) (One-pot Synthesis) Compounds (XI-2, E-Isomer and XI-2, Z-Isomer)

5 g (0.0197 mol) of N-methyl-E/Z-2-(2-hydroxyphenyl)-2-methoxyiminoacetamide mixture (in particular Example I-1f; HPLC: 37.9% E, log p=0.98; 44% Z, log p=1.29) are dissolved in 100 ml of acetonitrile and, after addition of 3.65 g (0.0264 mol) of potassium carbonate, the mixture is stirred at room temperature for 30 minutes. 5.87 g (0.0242 mol) of 4-(2'-chlorophenoxy)-5,6-difluoropyrimidine are added dropwise to the reaction mixture, and the mixture is stirred at room temperature for 12 hours. The mixture is subsequently heated under reflux for 3 hours. The mixture is poured into water and extracted 3 times with 100 ml of diethyl ether, and the organic phase is dried over sodium sulphate, saturated with hydrogen chloride and allowed to stand at room temperature for 24 hours. The mixture is then poured into water and the organic phase is dried over sodium sulphate.

The residue is triturated with diethyl ether and filtered off. This gives 4.9 g of crystals which, according to HPLC, contain 97.6% N-methyl-E-2-[2-(5-fluoro-2'-chlorophenoxypyrimidin-4-yloxy)phenyl]-2-methoxyiminoacetamide (XI-2, E-isomer) of log p=3.01 and 0.74% N-methyl-Z-2-[2-(5-fluoro-2'-chlorophenoxypyrimidin-4-yloxy)-phenyl]-2-methoxyiminoacetamide (XI-2, Z-isomer) of log p=2.94. The mother liquor is concentrated under reduced pressure, giving 2.6 g of a product containing 10.9% E product (XI-2, E-isomer) of log p=3.01 and 17.2% Z product (XI-2, Z-isomer) of log p=2.94.

III. Further Examples for the Isomerization of Compounds of the General Formula (XI)

1. N-Methyl-E-2-[2-(5-fluoro-2'-methyl-3'-chlorophenoxy-pyrimidin-4-yloxy)phenyl]-2-methoxyiminoacetamide (XI-1, E-isomer)

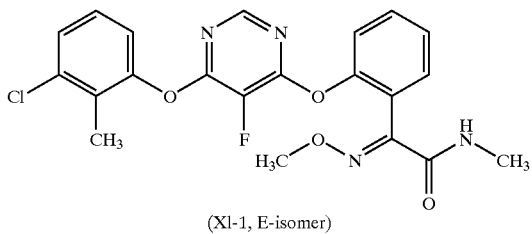

(XI-1, E-isomer)

Isomerization of N-Methyl-Z-2-[2-(5-fluoro-2'-methyl-3'-chlorophenoxy-pyrimidin-4-yloxy)-phenyl]-2-methoxyiminoacetamide (XI-1, Z-Isomer) to N-Methyl-E-2-[2-(5-fluoro-2'-methyl-3'-chlorophenoxy-pyrimidin-4-yloxy)phenyl]-2-methoxyiminoacetamide (XI-1, E-Isomer)

Toluene (10 ml) is saturated at room temperature with hydrogen chloride gas and subsequently treated with N-methyl-Z-2-[2-(5-fluoro-2'-methyl-3'-chlorophenoxypyrimidin-4-yloxy)-phenyl]-2-methoxyiminoacetamide (XI-1, Z-isomer) (0.5 g, content (Z+E): 99.3%, Z/E=99/1). The mixture is stirred 24 hours at room temperature, the solvent is destined of, giving N-methyl-E-2-[2-(5-fluoro-2'-methyl-3'-chlorophenoxypyrimidin-4-yloxy)phenyl]-2-methoxyiminoacetamide (XI-1, E-isomer) (0.5 g, content (E+Z): 98.3%, HPLC E/Z=92/8).

2. N-Methyl-E-2-[2-(5-fluoro-2'-methyl-3'-chlorophenoxy-pyrimidin-4-yloxy)phenyl]-2-methoxyiminoacetamide (XI-1, E-Isomer)

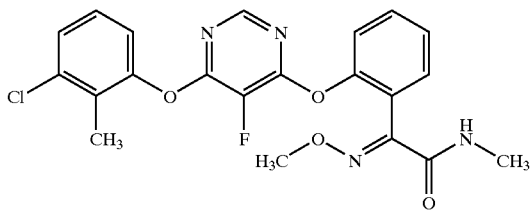

(XI-1, E-isomer)

Isomerization of N-Methyl-Z-2-[2-(5-fluoro-2'-methy-3'-chlorophenoxy-pyrimidin-4-yloxy)-phenyl]-2-methoxyiminoacetamide (XI-1, Z-Isomer) to N-Methyl-E-2-[2-(5-fluoro-2'-methyl-3'-chlorophenoxy-pyrimidin-4-yloxy)phenyl]-2-methoxyiminoacetamide (XI-1, E-Isomer)

N-methyl-Z-2-[2-(5-fluoro-2'-methyl-3'-chlorophenoxypyrimidin-4-yloxy)-phenyl]-2-methoxyiminoacetamide (XI-1, Z-isomer) (0.5 g, content (Z+E): 99.3%, Z/E=99/1) (XI-1, Z-isomer) is suspended in ethyl acetate (9.5 g) and treated with concentrated sulfuric acid (0.5 g). The mixture is stirred at room temperature for 20 hours, the solvent is distilled off under reduced pressure, the residue is taken up in methylene chloride/water, the organic phase is separated and dried over sodium sulphate. After distilling of the solvent this gives N-methyl-E-2-[2-(5-fluoro-2'-methyl-3'-chlorophenoxypyrimidin-4-yloxy) phenyl]-2-methoxyiminoacetamide (XI-1, E-isomer)) (0.4 g, content (E+Z): 98.4%, HPLC E/Z=96/4).

The determination of the logP-Values was carried out for all examples according to the EEC-Direktive 79/831 Annex V. A8 by HPLC (gradient method, acetonitrile/0,1% aqueous phosphoric acid).

What is claimed is:

1. A process for preparing a compound of the Formula (I),

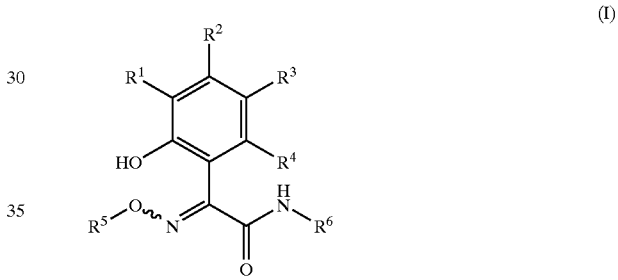

in which
R$^1$, R$^2$, R$^3$ and R$^4$ are identical or different and independently of one another each represents hydrogen, halogen, cyano, nitro, in each case optionally halogen-substituted alkyl, alkoxy, alkylthio, alkylsulphinyl or alkylsulphonyl, R$^5$ represents substituted or unsubstituted alkyl, R$^6$ represents hydrogen, substituted or unsubstituted alkyl, selected from the group of processes A, B, C and D, defined below wherein said process A comprises in a process step (2), the step of reacting in the presence of an acid or an acidic ion exchanger a compound of the Formula (IV),

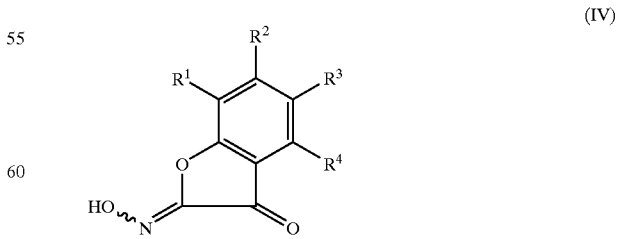

in which
R$^1$, R$^2$, R$^3$ and R$^4$ are as defined above,
with an alcohol of the Formula (V), $$R^7-OH \quad (V)$$

in which
R⁷ represents substituted or unsubstituted alkyl, and with a carbonyl compound, which binds hydroxylammonium chloride eliminated in the reaction forming an oxime, to give a compound of the Formula (VI),

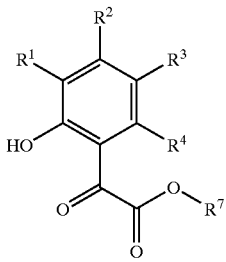

(VI)

in which
R¹, R², R³, R⁴ and R⁷ are as defined above,
and the resulting compound of the Formula (VI) is either
a) according to a process step (3), reacted with a hydroxylammonium salt, optionally in the presence of a diluent and optionally in the presence of an acid or an acid acceptor, to give a compound of the Formula (VII),

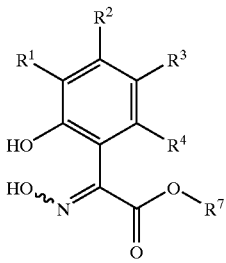

(VII)

in which
R¹, R², R³, R⁴ and R⁷ are as defined above,
and the resulting compound of the Formula (VII) is, according to a process step (4), reacted with an alkylating agent of the Formula (VIII), $$R^5-X \quad (VIII)$$

in which
R⁵ is as defined above and
X represents halogen or —O—SO₂—O—R⁵, where R⁵ is as defined above, optionally in the presence of a diluent and optionally in the presence of a base, or
b) according to a process step (5), reacted with an alkoxyamine of the Formula (IX), $$R^5-O-NH_2 \quad (IX)$$

in which
R⁵ is as defined above,
or an acid addition complex thereof, optionally in the presence of a diluent and optionally in the presence of an acid or an acid acceptor, and, wherein said process B comprises in a process step (6), the step of reacting a compound of the Formula (IV),

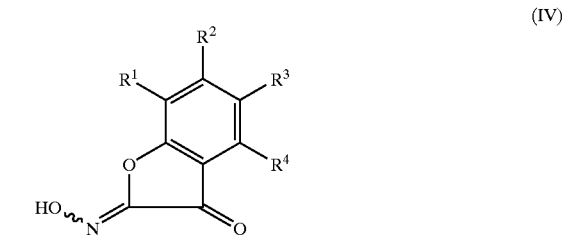

(IV)

in which
R¹, R², R³ and R⁴ are as defined above, with an alkoxyamine of the Formula (IX), $$R^5-O-NH_2 \quad (IX)$$

in which
R⁵ is as defined above,
or an acid addition complex thereof optionally in the presence of a diluent and optionally in the presence of an acid, and
wherein said process C comprises in a process step (7), the step of reacting in the presence of an acid or an acidic ion exchanger a compound of Formula (IV),

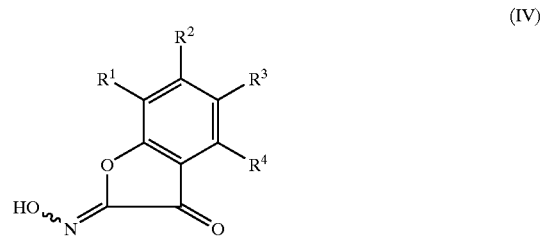

(IV)

in which
R¹, R², R³ and R⁴ are as defined above, with
an alcohol of the Formula (V), $$R^7-OH \quad (V)$$

in which R⁷ is as defined above,
optionally with addition of a hydroxylammonium salt, and the resulting compound of the Formula (VII),

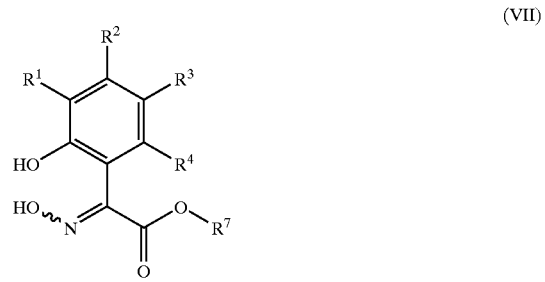

(VII)

in which
R¹, R², R³, R⁴ and R⁷ are as defined above,
is reacted according to said process step (4), and
wherein said process D comprises in a process step (8), the step of reacting in the presence of an acid or an acidic ion exchanger a compound of the Formula (X),

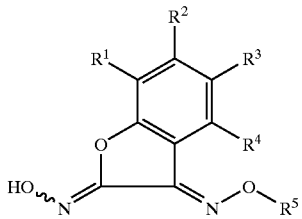
(X)

in which

R¹, R², R³, R⁴ and R⁵ are as defined above, with an alcohol of the Formula (V),

 (V)

in which R⁷ is as defined above, optionally in the presence of a carbonyl compound which binds hydroxylammonium chloride eliminated in the reaction forming an oxime, and wherein the compound of the Formula (II) obtained according to any of said processes A through D,

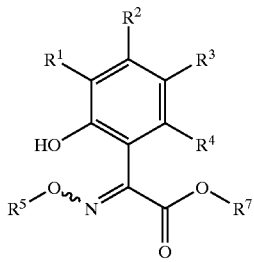
(II)

in which

R¹, R², R³, R⁴ and R⁵ are as defined above and

R⁷ represents unsubstituted or substituted alkyl, is, optionally reacted according to a process step (1) without intermediate isolation of the compound of the Formula (II) from a reaction vessel (one-pot process), with an alkylamine of the Formula (III),

 (III)

in which

R⁶ is as defined above, optionally in the presence of a diluent.

2. A process for preparing a compound of the Formula (XI),

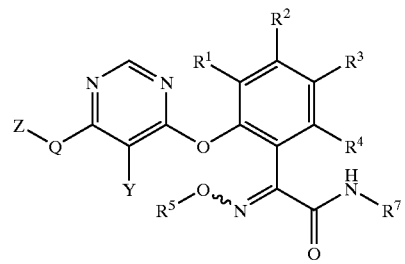
(XI)

in which

Z represents unsubstituted or substituted cycloalkyl, aryl or heterocyclyl,

Q represents oxygen or sulphur,

Y represents halogen,

R¹, R², R³ and R⁴ are identical or different and independently of one another each represents hydrogen, halogen, cyano, nitro, in each case optionally halogen-substituted alkyl, alkoxy, alkylthio, alkylsulphinyl or alkylsulphonyl, R⁵ represents substituted or unsubstituted alkyl and R⁷ represents unsubstituted or substituted alkyl, comprising the steps of:

preparing a compound of the Formula (I) according to claim 1, and, reacting said compound of the Formula (I) with either E) according to a process step (9) a pyrimidine derivative of the Formula (XII),

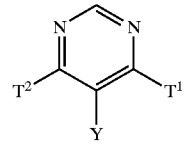
(XII)

in which

T¹ and T² are identical or different and represent halogen and Y is as defined above, optionally in the presence of a diluent and optionally in the presence of a base, and the resulting compound of the Formula (XIII),

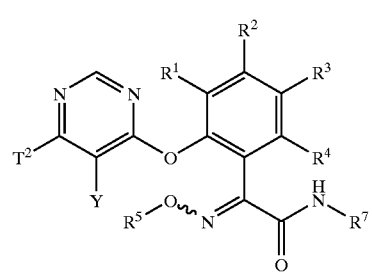
(XIII)

in which

T², Y, R¹, R², R³, R⁴, R⁵ and R⁷ are as defined above, is reacted, according to a process step (10), with a cyclic compound of the Formula (XIV),

 (XIV)

in which
Z and Q are as defined above,
optionally in the presence of a diluent and optionally in the presence of an acid acceptor and optionally in the presence of a catalyst, or
F) according to a process step (11) with a compound of the Formula (XV),

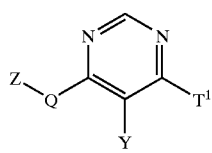

(XV)

in which
Z, Q, T¹ and Y are as defined above,
optionally in the presence of a diluent and optionally in the presence of a base.

3. A compound of the Formula (VII),

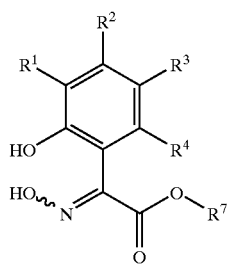

(VII)

in which
R¹, R², R³, R⁴ and R⁷ are as defined in claim 1, except for the compound (VII-a)

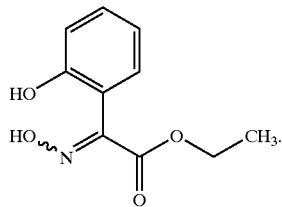

(VII-a)

4. A method for preparing a compound of the Formula (I) as defined in claim 1 comprising the steps of:
preparing a compound of the Formula (VII) as defined in claim 3, and employing said compound of the Formula (VIII) as an intermediate in the preparation of a compound of the Formula (I) as defined in claim 1.

5. The process according to claim 1, wherein said process A, subpart b comprising said process steps (2), (5), and (1) are carried out as a one-pot process.

6. The process according to claim 1, wherein the diluent used in all process steps is methanol.

7. The process according to claim 1, wherein the alkylating agent is methyl chloride.

8. The process according to claim 2, wherein said process step (2) is carried out in a one-pot process.

9. A process for isomerizing a compound of the Formula (XI),

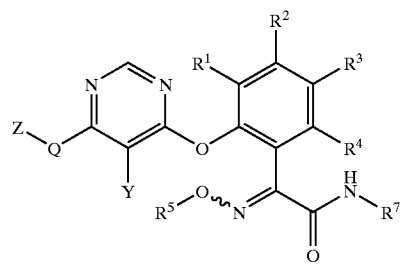

(XI)

in which

Z represents unsubstituted or substituted cycloalkyl, aryl or heterocyclyl,

Q represents oxygen or sulphur,

Y represents halogen,

R¹, R², R³ and R⁴ are identical or different and independently of one another each represents hydrogen, halogen, cyano, nitro, in each case optionally halogen-substituted alkyl, alkoxy, alkylthio, alkylsulphinyl or alkylsulphonyl, R⁵ represents substituted or unsubstituted alkyl and R⁷ represents unsubstituted or substituted alkyl, comprising the step of reacting a compound of the Formula (XI) with an acid, optionally in a diluent.

10. The process for preparing said compound of the Formula (IX) according to claim 2, further comprising the step of isomerizing said compound of the Formula (XI) with said isomerization process of claim 9, wherein said isomerization process is carried out after said process step (2).

11. A process for preparing a compound of the Formula (VI),

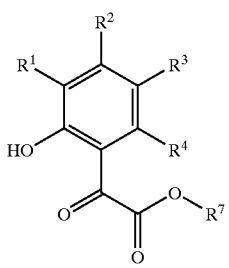

(VI)

in which

R¹, R², R³ and R⁴ are identical or different and independently of one another each represents hydrogen, halogen, cyano, nitro, in each case optionally halogen-substituted alkyl, alkoxy, alkylthio, alkylsulphinyl or alkylsulphonyl and R⁷ represents unsubstituted or substituted alkyl, comprising the step of:
reacting in the presence of an acid or an acidic ion exchanger a compound of the Formula (IV),

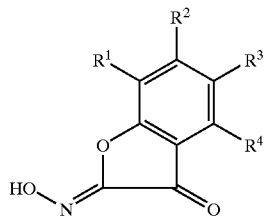

(IV)

in which

R¹, R², R³ and R⁴ are as defined above, with an alcohol of the Formula (V),

 (V)

in which R⁷ is as defined above and with a carbonyl compound which binds hydroxylammonium chloride eliminated in the reaction forming an oxime.

12. A process for isomerizing a compound of the Formula (XIII),

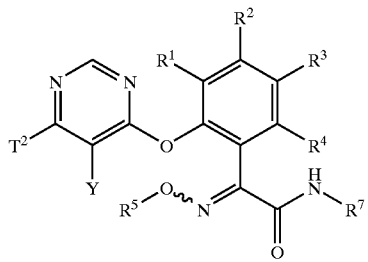

(XIII)

in which

T² represents halogen,

Y represents halogen,

R¹, R², R³ and R⁴ are identical or different and independently of one another each represents hydrogen, halogen, cyano, nitro, in each case optionally halogen-substituted alkyl, alkoxy, alkylthio, alkylsulphinyl or alkylsulphonyl, R⁵ represents substituted or unsubstituted alkyl and R⁷ represents unsubstituted or substituted alkyl, comprising the step of reacting a compound of the Formula (XIII) with an acid, optionally in a diluent.

* * * * *